(12) United States Patent
Foley et al.

(10) Patent No.: US 7,608,096 B2
(45) Date of Patent: Oct. 27, 2009

(54) POSTERIOR PEDICLE SCREW AND PLATE SYSTEM AND METHODS

(75) Inventors: Kevin T. Foley, Germantown, TN (US); Aure Bruneau, Memphis, TN (US); Anthony J. Melkent, Germantown, TN (US); Thomas E. Roehm, III, Braden, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 485 days.

(21) Appl. No.: 10/385,396

(22) Filed: Mar. 10, 2003

(65) Prior Publication Data

US 2004/0177847 A1    Sep. 16, 2004

(51) Int. Cl.
*A61B 17/70* (2006.01)
(52) U.S. Cl. ..................................... 606/280
(58) Field of Classification Search .............. 606/60, 606/61, 69, 72, 73, 280–297
See application file for complete search history.

(56) References Cited

U.S. PATENT DOCUMENTS

| | | | |
|---|---|---|---|
| 1,025,008 A | 4/1912 | Miner | |
| 2,443,363 A | 6/1948 | Townsend et al. | |
| 3,742,583 A | 7/1973 | Devlin et al. | |
| 4,408,601 A | 10/1983 | Wenk | |
| 4,513,744 A | 4/1985 | Klaue | |
| 4,763,644 A | 8/1988 | Webb | |
| 4,805,602 A | 2/1989 | Puno et al. | |
| 4,836,196 A | 6/1989 | Park et al. | |
| 4,946,458 A | 8/1990 | Harms et al. | |
| 5,005,562 A | 4/1991 | Cotrel | |
| 5,084,048 A | 1/1992 | Jacob et al. | |
| 5,129,899 A | 7/1992 | Small et al. | |
| 5,176,678 A | 1/1993 | Tsou | |
| 5,207,678 A | 5/1993 | Harms et al. | |
| 5,209,751 A | 5/1993 | Farris et al. | |
| 5,217,497 A | 6/1993 | Mehdian | |
| 5,234,431 A | 8/1993 | Keller | |
| 5,261,909 A | 11/1993 | Sutterlin et al. | |
| 5,261,910 A | 11/1993 | Warden et al. | |

(Continued)

FOREIGN PATENT DOCUMENTS

DE        37 11013 C1    9/1988

(Continued)

OTHER PUBLICATIONS

Protest under 37 C.F.R. Section 1.291, dated Mar. 3, 1997.

(Continued)

*Primary Examiner*—Corrine M McDermott
*Assistant Examiner*—Christopher D Prone

(57) ABSTRACT

An apparatus is provided for correcting spinal abnormalities, and particularly for providing compression and/or distraction of vertebrae without additional tools or instrumentation. A plate member is provided with a plurality of slots, one of which has a sloped internal edge or surface. The plate is anchored to one vertebra by a first anchor, and a second anchor is then placed through the slot with the sloped internal edge or surface and tightened. Such tightening causes the plate to move with respect to the tightened anchor, and thus to transmit compression or distraction to the vertebrae. The apparatus is particularly useful in minimally-invasive surgeries but can also be used in more traditional open surgeries.

21 Claims, 6 Drawing Sheets

U.S. PATENT DOCUMENTS

| | | | |
|---|---|---|---|
| 5,304,179 A | 4/1994 | Wagner | |
| 5,346,493 A | 9/1994 | Stahurski et al. | |
| 5,360,431 A | 11/1994 | Puno et al. | |
| 5,364,399 A | 11/1994 | Lowery et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,486,174 A | 1/1996 | Fournet-Fayard et al. | |
| 5,501,684 A | 3/1996 | Schlapfer et al. | |
| 5,520,690 A | 5/1996 | Errico et al. | |
| 5,531,745 A | 7/1996 | Ray | |
| 5,531,746 A | 7/1996 | Errico et al. | |
| 5,545,163 A | 8/1996 | Miller et al. | |
| 5,549,608 A | 8/1996 | Errico et al. | |
| 5,554,157 A | 9/1996 | Errico et al. | |
| 5,562,661 A | 10/1996 | Yoshimi et al. | |
| 5,575,792 A | 11/1996 | Errico et al. | |
| 5,578,033 A | 11/1996 | Errico et al. | |
| 5,582,612 A | 12/1996 | Lin | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,603,713 A | 2/1997 | Aust et al. | |
| 5,607,426 A | 3/1997 | Ralph et al. | |
| 5,609,593 A | 3/1997 | Errico et al. | |
| 5,609,594 A | 3/1997 | Errico et al. | |
| 5,613,967 A | 3/1997 | Engelhardt et al. | |
| 5,647,873 A | 7/1997 | Errico et al. | |
| 5,669,911 A | 9/1997 | Errico et al. | |
| 5,672,176 A | 9/1997 | Biedermann et al. | |
| 5,681,311 A | 10/1997 | Foley et al. | |
| 5,688,273 A | 11/1997 | Errico et al. | |
| 5,690,630 A | 11/1997 | Errico et al. | |
| 5,697,929 A | 12/1997 | Mellinger | |
| 5,733,286 A | 3/1998 | Errico et al. | |
| 5,735,853 A | 4/1998 | Olerud | |
| 5,743,907 A * | 4/1998 | Asher et al. | 606/61 |
| 5,782,833 A | 7/1998 | Haider | |
| 5,797,911 A | 8/1998 | Sherman et al. | |
| 5,797,912 A | 8/1998 | Runciman et al. | |
| 5,810,817 A | 9/1998 | Roussouly et al. | |
| 5,810,823 A | 9/1998 | Klaue et al. | |
| 5,817,094 A | 10/1998 | Errico et al. | |
| 5,879,350 A | 3/1999 | Sherman et al. | |
| 5,882,350 A | 3/1999 | Ralph et al. | |
| 5,885,286 A | 3/1999 | Sherman et al. | |
| 5,891,145 A | 4/1999 | Morrison et al. | |
| 5,984,924 A | 11/1999 | Asher et al. | |
| 6,053,917 A | 4/2000 | Sherman et al. | |
| 6,063,090 A | 5/2000 | Schlapfer | |
| 6,066,140 A | 5/2000 | Gertzbein et al. | |
| 6,248,105 B1 | 6/2001 | Schläpfer et al. | |
| 6,280,445 B1 | 8/2001 | Morrison et al. | |
| 6,287,309 B1 | 9/2001 | Baccelli et al. | |
| 6,315,779 B1 | 11/2001 | Morrison et al. | |
| 6,461,359 B1 * | 10/2002 | Tribus et al. | 606/61 |
| 6,530,926 B1 | 3/2003 | Davison | |
| 6,648,885 B1 * | 11/2003 | Friesem | 606/61 |
| 6,689,133 B2 | 2/2004 | Morrison et al. | |
| 2001/0047172 A1 * | 11/2001 | Foley et al. | 606/69 |
| 2004/0176763 A1 | 9/2004 | Foley et al. | |

FOREIGN PATENT DOCUMENTS

| | | |
|---|---|---|
| DE | 195 09 332 | 8/1996 |
| DE | 197 20 782 A1 | 11/1998 |
| FR | 2 758 971 A1 | 8/1998 |
| FR | 2 763 828 | 12/1998 |
| GB | 2 173 104 A | 10/1996 |

OTHER PUBLICATIONS

Declaration of J.P. Errico Pursuant To Protest Under 37 C.F.R. Section 1.291.

Sofamor Danek Meeting May 2, 1996, entitled Implemedics.

* cited by examiner

POSTERIOR PEDICLE SCREW AND PLATE SYSTEM AND METHODS

FIELD OF THE INVENTION

The present invention relates to an orthopedic implant assembly for use in stabilizing bone members in a desired spatial relationship in correcting bone misalignment disorders or for spinal or other bone fusion. In particular, the invention concerns a multi-axial spinal fixation system incorporating an elongated member such as a plate.

BACKGROUND OF THE INVENTION

In the art of orthopedic surgery, and particularly in spinal surgery, it has long been known to affix an elongated member, such as a plate or rod, to bones in order to hold them and support them in a given position. For example, in a procedure to fuse damaged, diseased, malformed, or otherwise abnormal vertebrae, the vertebrae are positioned in a corrected position by a surgeon. An elongated plate is placed adjacent to the vertebral bone, and bone anchors, such as specially-configured screws or bolts, are employed to secure the plate to the bones. With such anchors, placement is accomplished by drilling one or more holes in the bone(s) and threading the anchors into the holes. As examples, see U.S. Pat. No. 5,676,666 to Oxland et al., U.S. Pat. No. 5,613,967 to Engelhardt et al., and U.S. Pat. No. 5,603,713 to Aust et al. An anchor can be connected to the bone, as by threading into a vertebral hole, through a plate, or alternatively the plate can be placed in position over or around the anchor after the anchor is connected to the bone. The anchor and plate are then secured to each other to minimize or prevent relative movement. In this way, bones may be spinal held and/or supported in proper alignment for healing.

It has been found desirable for implant systems to have the capability for angular orientation of a bolt or other anchor in multiple planes relative to the elongated member or other fixation mechanisms of the implant system. Such features enable bone anchors to be placed at angles which are optimal for anchoring, thus reducing the chance of loosening, pull-out, or other movement of the anchors while not compromising the optimal positioning of the fixation plate.

Additionally, such systems alleviate awkwardness frequently found in spinal surgery due to uneven bone surfaces and the abnormality to be corrected and generally require less adjustment to the implant, rendering corrective surgery easier for the surgeon and less traumatic for the patient.

Various approaches have been used to achieve such multi-axial capability. For example, U.S. Pat. No. 5,735,853 to Olerud discloses an implant device in which a bone bolt can occupy different angular positions in relation to a plate by providing a compressible spherical collar which snap-fits around the bolt, which collar is rotatable and tiltable in a spherical opening in a plate insert. The compression fit of the bolt and collar within the plate can present difficulty in assembling the apparatus, particularly in a fluid-prevalent environment.

Another approach is shown in U.S. Pat. No. 5,304,179 to Wagner, which shows a bone screw fixed inside a bushing at an angle with respect to the longitudinal axis of the bushing. The bushing is rotatable within a portion of a connector angled with respect to the axis of the adjoining rod-based instrumentation. The connector is rotatable around the instrumentation axis. The Wagner system permits only discrete positions of a bone screw in three-dimensional space to be achieved, and the bushings add extra length and profile to the construct, as well as extra parts for the surgeon to handle and arrange.

A third approach is shown in U.S. Pat. No. 5,984,924 to Asher et. al., which shows a bone alignment system having an elongated bone alignment member sandwiched between two pairs of washers. Each such pair of washers have corresponding surfaces that mate together in a "ball and socket" configuration to potentially occupy a plurality of positions. When the shaft of a bone anchor extends through each washer pair, and also through an aperture of the elongated member, the washer pairs enable the shaft to be oriented at various angles relative to the elongated member. This approach also requires a plurality of small parts for handling and assembly during surgery. Further, since the washers in that system lie outside of the elongated member, they increase the thickness of the overall construct, with the attendant increase in the difficulty of use in a small surgical space and in the potential for patient discomfort.

As noted above, in placing such implants a surgeon is commonly required to reposition vertebrae so that a normal spinal curvature results from the surgery. In open surgical procedures, the surgeon may reposition vertebra(e) manually or may have tools to assist in the repositioning. Once the vertebrae are repositioned, implants can then be attached in order to hold the vertebrae in the desired position. Alternatively, it is also known to provide a rod that is pre-bent to approximate a normal spinal curvature and to provide hooks or screws that can hold the rod which attach to several vertebrae. With such apparatus, vertebrae can be repositioned by forcing the pre-bent rod into engagement with the hooks or screws that are already anchored in the vertebrae. Even with that method, however, additional tools such as a rod reducer are required. For example, to compress (i.e., push together) or distract (i.e., push apart) two vertebrae, it is known to use, among other relatively large tools, a scissors- or tongs-like device by squeezing or pulling apart on handles of such a tool; distal parts of the tool that contact vertebrae or devices attached to vertebrae will cause the distraction or compression.

Performing these tasks using traditional techniques and devices of open surgery has several undesirable features and consequences. Initially, such open surgery requires a long incision which leaves a relatively long and unappealing scar. Further, such surgery entails incision, retraction, and adjustment of numerous tissues in addition the spinal tissues. As a result, trauma to these tissues and resulting pain and possibility of infection are relatively high. Still further, a standard thoracotomy or other incision may expose only one apex of the spinal curve to be corrected, thus requiring additional long incisions or a longer initial incision in order to be able to fully treat the spine. Even where the apex of the spinal curve is adequately exposed and in good position relative to the thoracotomy for surgery, commonly adjacent vertebrae and intervertebral discs are not parallel to the exposure view provided by the incision, decreasing the effectiveness of instrumentation used to correct the abnormal curvature. For these reasons, an endoscopic, thoracoscopic, or other minimally-invasive approach is preferable.

Accordingly, there remains a need for a device that simplifies adjustment or repositioning of vertebrae, particularly when a minimally-invasive approach is used.

SUMMARY OF THE INVENTION

In one embodiment, an apparatus is disclosed comprising a plate member having a curvature, a first slot and a second slot, and sized to be inserted into the body through a minimally-invasive, open or other surgical opening. The slots each have a side wall sized to accommodate at least a portion of a bone anchor. A sloped surface is provided within said second slot, with the surface sloping in a longitudinal direction. A first bone fixation element that is adapted to engage the plate member is also provided, wherein at least a part of the first bone fixation element is capable of being within the first slot. A second bone fixation element is adapted to engage the plate member within the second slot along the sloped surface, whereby tightening the second bone fixation element after engagement with the sloped surface causes the plate member to move with respect to the second bone fixation element.

In specific embodiments, the curvature of the plate member may approximate a natural curvature of one or more spinal segments, such as a lordotic or kyphotic curvature. The sloped surface may slope approximately uniformly, may be integrally formed as a part of the wall of the slot, and may have a downward or upward slope (viewed from an end of the second slot near an end of the plate member toward the end of the second slot in the middle of the plate member). A part of the surface may have no slope, i.e., may be substantially parallel to the bottom of the plate member. A bone fixation element retainer (e.g. a set screw) may be provided connected to the plate member (e.g. via a threaded hole) adjacent the second slot. The bone fixation elements may be part of a multi-axial bone fixation apparatus, standard bone screws, or screws having a head portion with a rounded underside and a diameter larger than a distance between adjacent portions of the sloped surface. The apparatus can further include additional slots sized to accommodate at least a portion of a bone anchor, and bone anchors for such slots.

In another embodiment, a kit is provided comprising at least one plate member, each having a curvature, a first slot, a second slot and a sloped surface within said second slot. The said surface slopes in a longitudinal direction, and the plate member(s) are sized to be inserted into the body through a minimally-invasive, open or other surgical opening. Also provided is at least one first bone fixation element, each adapted to engage the plate member(s) and each having at least a part capable of being within the first slot, and at least one second bone fixation element, each adapted to engage the plate member(s) along the sloped surface. The kit may include a plurality of plate members not all of the same size and/or curvature, and some may have an upward slope while others have a downward slope. The plate members can be configured for attachment to the spine in one or more of the cervical, thoracic, lumbar, and sacral regions. The kit may also have a plurality of the first and/or second bone fixation elements adapted for attachment to the spine in one or more of the cervical, thoracic, lumbar, and sacral regions.

In yet another embodiment, a method is provided comprising providing a plate member having a curvature approximating a natural spinal lordosis curvature, a first slot and a second slot with a sloped surface formed within said second slot, and sized to be inserted into the body through a minimally-invasive, open or other surgical opening: inserting the plate member through the opening into a patient proximate to a vertebra to which the plate member is intended to be attached; placing a first anchoring member through the first slot and into a first vertebra; placing a second anchoring member through the second slot and into a second vertebra; and tightening the second anchoring member against the sloped surface so that the plate member moves with respect to the second anchoring member. The first anchoring member can be tightened with respect to said plate member prior to tightening the second anchoring member. The method can also include loosening the first and second anchoring members, adjusting the plate member along the vertebrae, and retightening the anchoring members. Tightening the second anchoring member can cause one of compression and distraction of vertebrae, and tightening can be ceased when a predetermined amount of one of compression and distraction of vertebrae has occurred.

In still another embodiment, a method of implanting a spinal implant having a lordosis curvature and a plurality of longitudinal slots, at least one of the slots having a surface slanted along the longitudinal direction, comprises making a minimally-invasive, open or other surgical opening proximate to first and second vertebrae in a patient: preparing a first hole in the first vertebra and a second hole in the second vertebra through the opening; inserting a first fixation member through the opening and into the first hole; inserting the implant through the opening and into a position adjacent the vertebrae such that the first fixation member is within one of the implant's slots and another of the slots in the implant is adjacent the second hole, that second slot including the slanted surface; inserting a second fixation member through the opening and through the second slot and into the second hole; and tightening the second fixation member such that it and the second vertebra move with respect to the implant.

DESCRIPTION OF THE PREFERRED EMBODIMENTS

Figure 1:
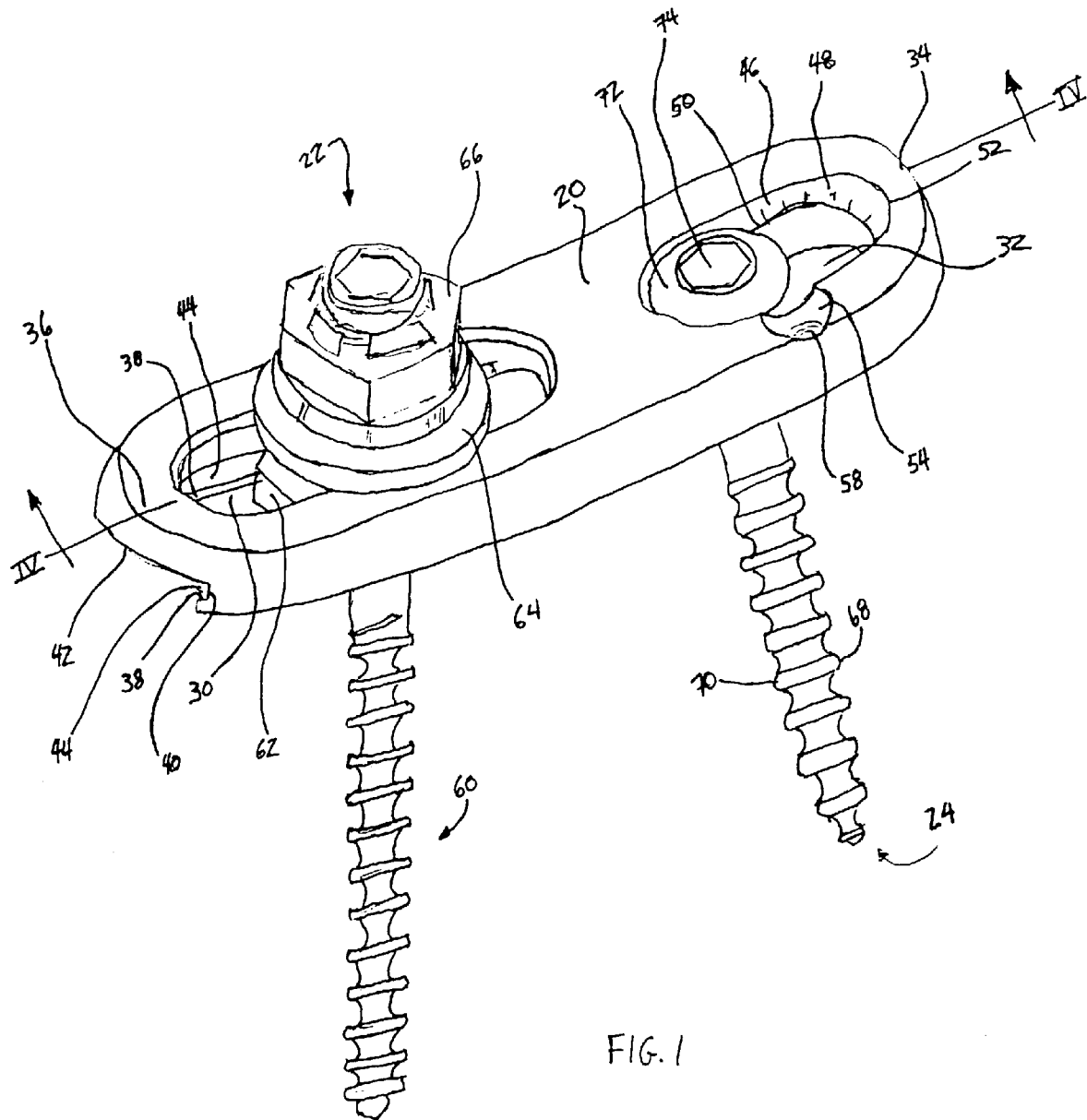
FIG. 1 is a perspective view of one embodiment of a device having features according to the present invention.
Figure 2:
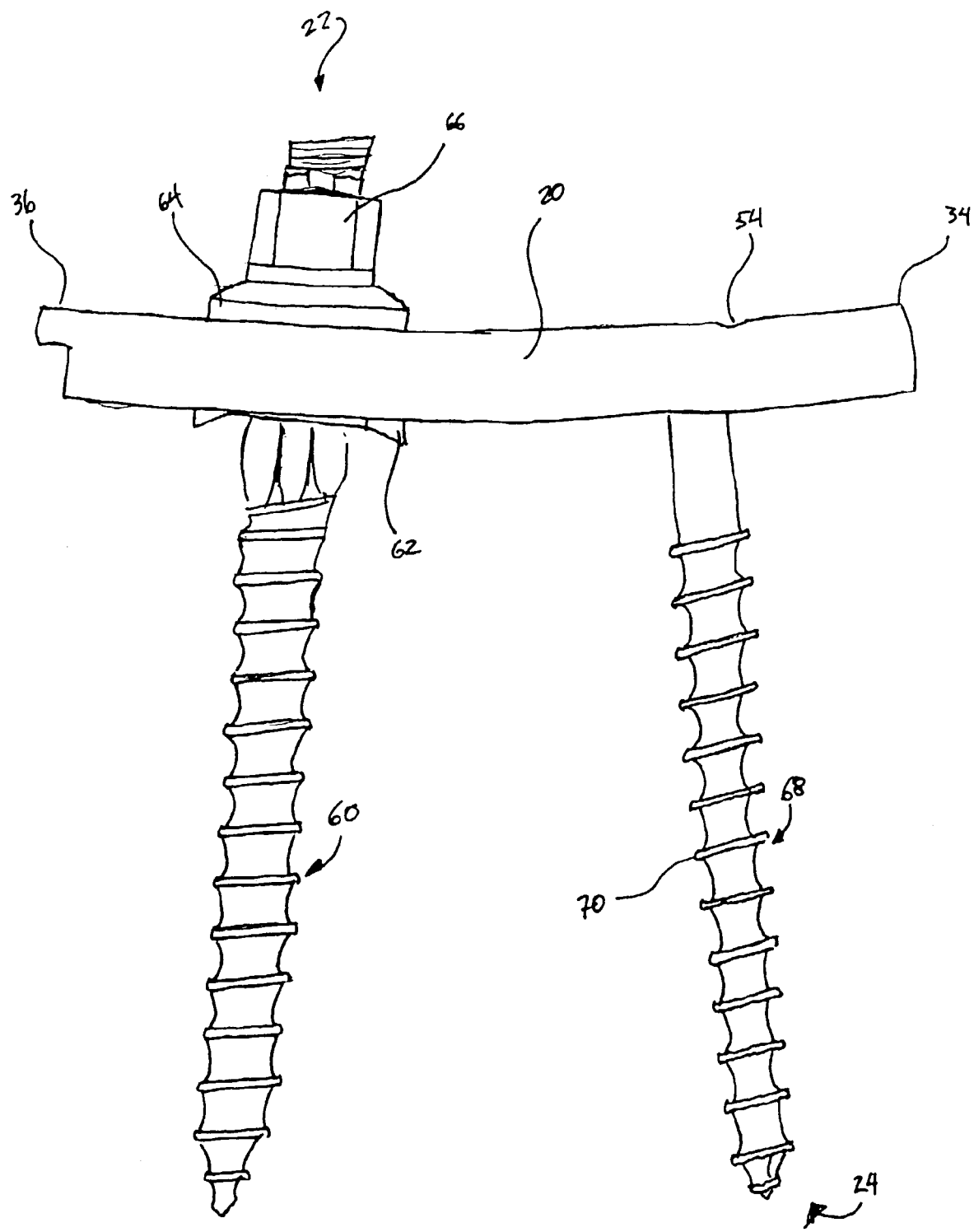
FIG. 2 is a side view of the embodiment illustrated in FIG. 1.
Figure 3:
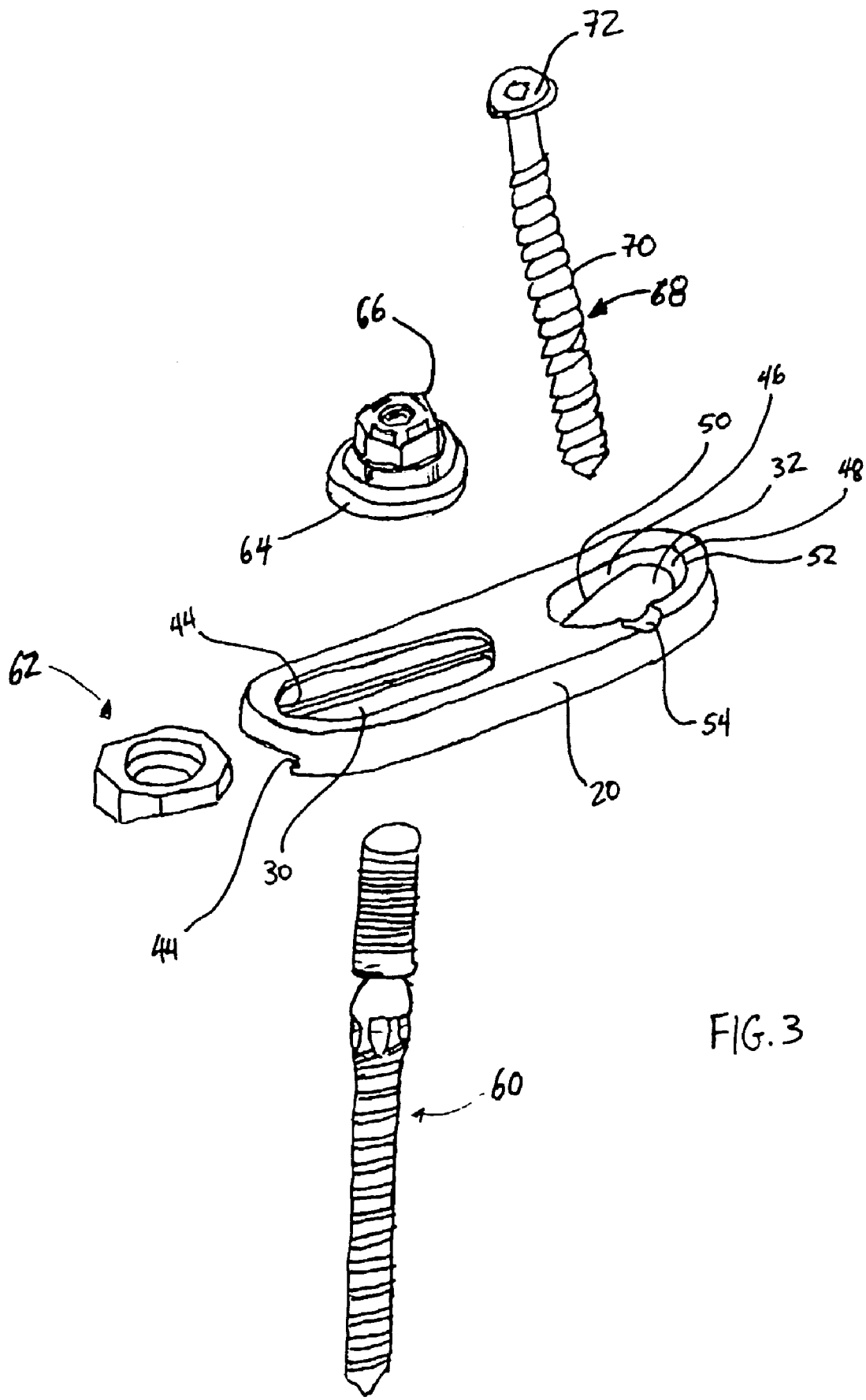
FIG. 3 is an exploded view of the embodiment illustrated in FIG. 1.
Figure 4:
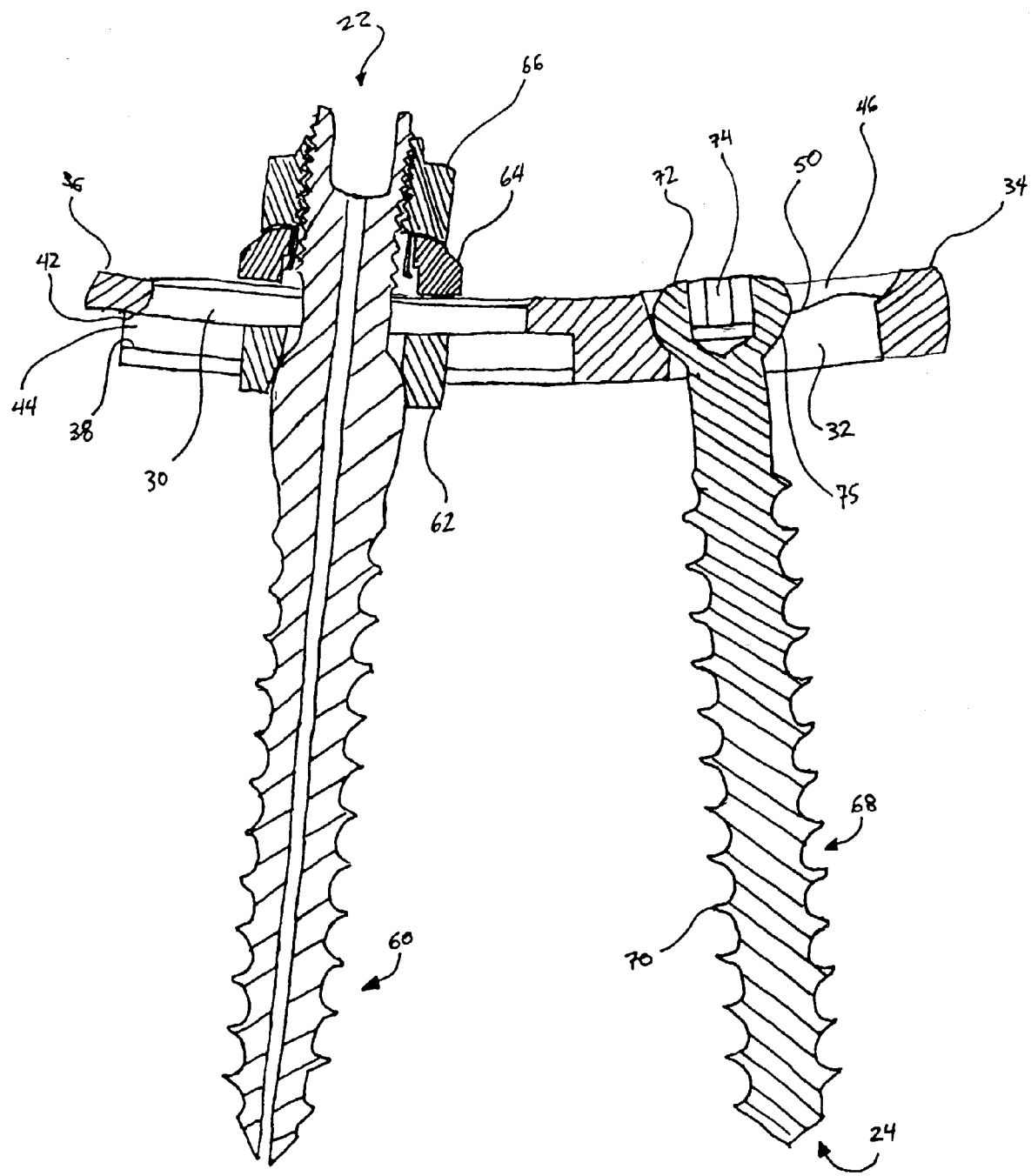
FIG. 4 is a cross section taken along the lines IV-IV in FIG. 1 and viewed in the direction of the arrows.
Figure 5:
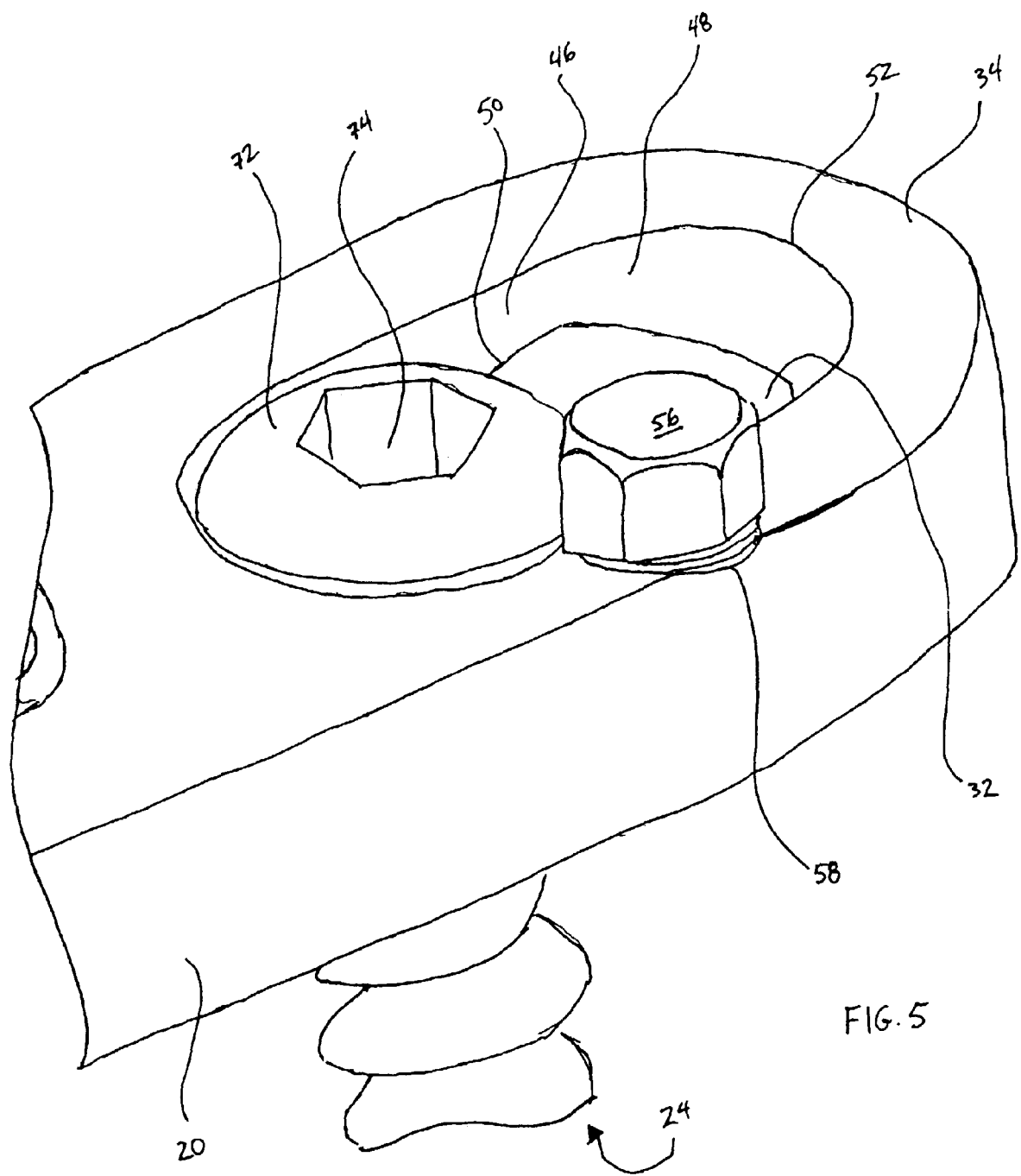
FIG. 5 is a magnified view of a portion of the embodiment illustrated in FIG. 1.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Referring now generally to FIGS. 1-5, there is shown a plate member 20 with a multi-axial bone fixation member 22 and a bone fixation member 24. Plate member 20 is elongated and includes a plurality of slots. In the illustrated embodiment, plate member 20 includes two slots 30 and 32, although it will be appreciated additional slots could be placed in plate member 20. In a particular embodiment, plate member 20 and slots 30 and 32 are sized so that plate member 20 can contact neighboring vertebrae, and slots 30 and 32 will each be adjacent one of those vertebrae so that fixation members can be placed through slots 30 and 32 and into the vertebrae. Plate member 20 may also be sized and configured to extend across more than two adjacent vertebrae.

In the illustrated embodiment, slot 32 is near a first end 34 of plate member 20, and slot 30 is near a second end 36 of plate member 20. Plate member 20, in the illustrated embodiment, is pre-bent or formed to include a curvature, for example a natural spinal lordosis curvature. As shown particularly in FIGS. 2 and 3, plate member 20 has a concave curvature, as viewed from the top. It will be understood that any curvature appropriate for one or more segments of the spine (whether cervical, thoracic, lumbar or sacral) could be incorporated into plate member 20. Such curvatures can include entirely convex, entirely concave, entirely straight (i.e. essentially planar), and combinations thereof. As noted previously, in the illustrated embodiment a lordosis curvature is depicted and is particularly a curvature characteristic of the lumbar spine. Plate member 20 could alternatively be part-lordotic with an uncurved portion, part-kyphotic with an uncurved portion, wholly kyphotic, or have another curvature or combination of curvatures.

In the illustrated embodiment, slot 30 is a longitudinal, oval-shaped slot. Slot 30 extends through plate member 20 from top to bottom. Proximate to the bottom of plate member 20, a ledge 38 extends into slot 30. Ledge 38, along with surfaces 40 and 42 of plate member 20, defines grooves 44 that run longitudinally along plate member 20 within slot 30. Grooves 44 accommodate a part of multi-axial bone fixation element 22, as will be described hereafter.

Slot 32 is also depicted in the illustrated embodiment as a longitudinal, oval-shaped slot. Slot 32 extends through plate member 20, from top to bottom. A sloped wall portion 46 extends into slot 32 and is preferably integral with plate member 20. In the illustrated embodiment, wall portion 46 has a concavely rounded portion 48 that ends in a sloping edge or surface 50. By "sloping," it is meant that points along edge or surface 50 are at different distances from the top surface of plate member 20 at different places along edge or surface 50, and may be approximately linear or have another suitable configuration. In the illustrated embodiment, a point along edge or surface 50 that is closer to first end 34 of plate member 20 than another point along edge or surface 50 will be closer to the top surface of plate member 20. It will be understood that edge or surface 50 may have a flat or non-sloped portion, that is, a portion that is substantially horizontal or parallel to a bottom surface of plate member 20. Such a portion in the present embodiment may preferably be adjacent the end of slot 32 that is toward a middle portion of plate member 20. In a specific embodiment, an upper edge 52 of slot 30 is sized so that the head of a bone screw or other fixation member (e.g., fixation member 24) will fit within edge 52, but edge or surface 50 will not allow the head of such a fixation member to pass.

The illustrated embodiment of plate member 20 further includes a hole 54 adjacent to slot 32. Hole 54 is for accommodating a retainer designed to hold fixation member 24 within slot 32, or to prevent fixation member 24 from backing out, such as set screw 56 (FIG. 5), a cam or sliding wedge member, a spring-loaded member or a similar device. In the embodiment in which set screw 56 is used, hole 54 will include a threaded portion 58. Hole 54 is preferably sized to accommodate at least a portion of the retainer (e.g., set screw 56), so that its top extends minimally or not at all over the top surface of plate member 20, thus reducing the profile of the overall construct.

Multi-axial fixation member 22 includes a bone bolt 60, a stabilizing member 62, a washer 64, and a nut 66. The respective elements of multi-axial fixation member 22 are described in detail in U.S. Pat. Nos. 6,280,445 and 6,315,779 to Morrison et al., and the entirety of those patents are incorporated herein by reference. In the illustrated embodiment, washer 64 and nut 66 are pre-attached, as is shown and described in U.S. Pat. No. 6,315,779. It will be appreciated that embodiments of the present invention are contemplated in which washer 64 and nut 66 are separate and are not associated with each other or in contact with each other until the attachment of multi-axial fixation member 22 to plate member 20.

Fixation member 24 is shown in one embodiment as a standard bone screw having an attachment portion 68 with cancellous threads 70, and a head portion 72. Head portion 72 includes a tool-engaging aperture 74, and preferably includes a rounded underside 75. As noted previously, the diameter of head portion 72 is preferably larger than the distance between sections of edge or surface 50 on opposite sides of slot 32, so that head portion 72 cannot pass through slot 32 in plate member 20.

For ease of use, a kit containing one or more of the parts of the implant may be provided. For example, a kit may include several embodiments of plate member 20, or one or more embodiments of plate member 20 in several different lengths, sizes and/or curvatures. Lengths or sizes appropriate for cervical, thoracic, lumbar and/or sacral implantation may be included. One or more sets of screws, bolts, stabilizers, washers, and/or nuts, preferably in a variety of sizes or adapted for attachment to one or more of the cervical, thoracic, lumbar and sacral regions of the spine, may also be provided in such a kit. For example, one or more fixation members 22 and/or 24 for engaging one or more slots in the plate members may be included. Further, retainers for holding fixation member 24 within slot 32 (e.g., set screw 56) may also be provided. In a specific embodiment of such a kit, each plate member 20 is provided with stabilizing member 62 preloaded into grooves 44 under slot 30. A catch, boss, or stop may be provided within grooves 44 or on stabilizing member 62 so that stabilizing member 62 cannot exit grooves 44 and fall out of plate member 20. Similarly, if washer 64 and nut 66 form an initial unit, as shown in U.S. Pat. No. 6,315,779, a variety of such units may be provided in the kit. Alternatively, separate quantities of nuts and washers can be provided.

A method of using the implant will now be described. As noted above, the implant can be used in minimally-invasive surgical procedures, and the methods described below reflect such procedures. It will be appreciated by those of skill in the art that the features that enable a minimally-invasive approach to be used with the implant will also make the implant easier to insert via a standard open or other surgical procedure.

Using a minimally-invasive technique, a surgeon will make an incision into the patient at a place relatively proximate to the vertebrae or other bone(s) to which the implant is to be attached. As is known in the art, a tube of sufficient length to extend to the implantation site from a point above the incision in the skin is inserted into the incision, and visual access to the site is obtained. After the appropriate access to the surgical site is obtained, a portion of the inferior vertebra to be instrumented (e.g. the pedicle) is prepared in a standard manner. For example, an awl may be used to prepare a hole, which is then probed for depth and tapped as appropriate for a bolt or screw element. Bolt 60 of the multi-axial bone fixation member 22 is then inserted into the hole in the inferior vertebra. Access to a portion of the superior vertebra (e.g. the pedicle) to be instrumented is then obtained, either via the previous incision or via a similar minimally-invasive incision. The point on the superior vertebra at which the implant is to be attached is identified, and the vertebra is prepared as described above. However, in the preferred embodiment, fixation member 24 is not yet inserted in the superior vertebra. Plate member 20 is then inserted (e.g., through the tube in the minimally-invasive incision). Plate member 20 is positioned over bone fixation member 22 and slot 30 is bottom-loaded (i.e. bone fixation member 22 is inserted into slot 30 through the bottom of plate member 20) so that bone fixation member 22 fits within slot 30. Plate member 20 is then translated or otherwise moved until the hole in the superior vertebra is adjacent slot 32. In one particular embodiment, the hole in the superior vertebra should be underneath the uppermost region of slot 32, i.e., the region closest to end 34 of plate member 20. Washer 64 and nut 66 are then placed on bolt 60, and nut 66 is tightened down onto washer 64 and plate member 20 to hold plate member 20 in position relative to the inferior vertebra. It will be noted that locking plate member in position can be performed solely by a nut 66, without an intermediary washer 64.

With plate member 20 locked with respect to the inferior vertebra, fixation member 24 can be top-loaded in plate member 20 (i.e. inserted through the top of plate member 20 and through slot 32) into the hole prepared in the superior vertebra. Fixation member 24 is inserted until its head portion 72 contacts sloped edge or surface 50 within slot 32. Fixation member 24 is then tightened further causing the plate member 20 to move with respect to fixation member 24. In effect, as fixation member 24 is tightened, plate member 20 slides in a direction parallel to slot 32 with respect to fixation member 24 and the superior vertebra, so that fixation members 22 and 24 approach each other. Since plate member 20 is locked with respect to fixation member 22 and the inferior vertebra, this sliding action causes the inferior and superior pedicles to be brought closer together, providing compression. Further, the curvature of the plate itself can provide correction to the curvature of the spine if it contacts the vertebrae as fixation member 24 is tightened with respect to plate member 20. Tightening of fixation member 24 can continue until the maximum amount of adjustment (e.g. compression) is obtained, or it can be discontinued when a predetermined amount of adjustment has occurred.

In many cases, the amount of compression or other correction of the vertebrae can be determined prior to surgery, and the positions of the holes in the vertebrae can be predetermined so that the vertebrae are in their proper, corrected positions when fixation member 24 is tightened to the extent that the head of fixation member 24 rests approximately at a point at which edge or surface 50 no longer slopes, or to the end of slot 32 that is toward the middle of plate member 20. In other words, commonly fixation member 24 can be tightened to a point where no further sliding action of plate member 20 with respect to fixation member 24 is possible. It will be appreciated, however, that in some cases proper correction will dictate that the tightening of fixation member 24 should stop even though head portion 72 of fixation member 24 has not yet reached the end of slot 32. When the tightening of fixation member 24 is complete, a retainer or anti-migration or holding element (such as set screw 56) can be inserted into aperture 54 or otherwise attached to plate member 20 adjacent fixation member 24 to cover and/or contact a portion (e.g. head portion 72) of fixation member 24.

If it is noted that the steps above do not provide adequate compression, fixation member 22 can be released, i.e., nut 66 can be loosened. Plate member 20 can then be adjusted by moving plate member 20 with respect to bolt 60 along slot 30, and nut 66 can then be retightened. In this way, end 34 of plate member 20 can be moved closer to the hole in the superior pedicle, resulting in the opportunity for more compression as fixation member 24 is tightened and plate member 20 slides a further distance with respect to fixation member 24. Similarly, if less compression is desired, plate member 20 should be positioned (or repositioned) such that the hole in the superior pedicle is closer to the end of slot 32 that is toward the middle of plate member 20. In a case in which no compression of the vertebrae is desired, plate member 20 should be positioned so that the hole in the superior pedicle is directly under the end of slot 32 closer to the middle of plate member 20, or so that the hole in the superior pedicle is over a relatively flat or non-sloped portion of edge 50.

As previously noted, the above-described technique is one preferred embodiment of a method of using the described implant. It should be noted that the technique can be reversed, that is, slot 32 can be adjacent an inferior vertebra and slot 30 can be adjacent a superior vertebra. Those with skill in the art will recognize that compression and/or distraction can also be obtained by using an additional external compression or distraction instrument.

Figure 6:
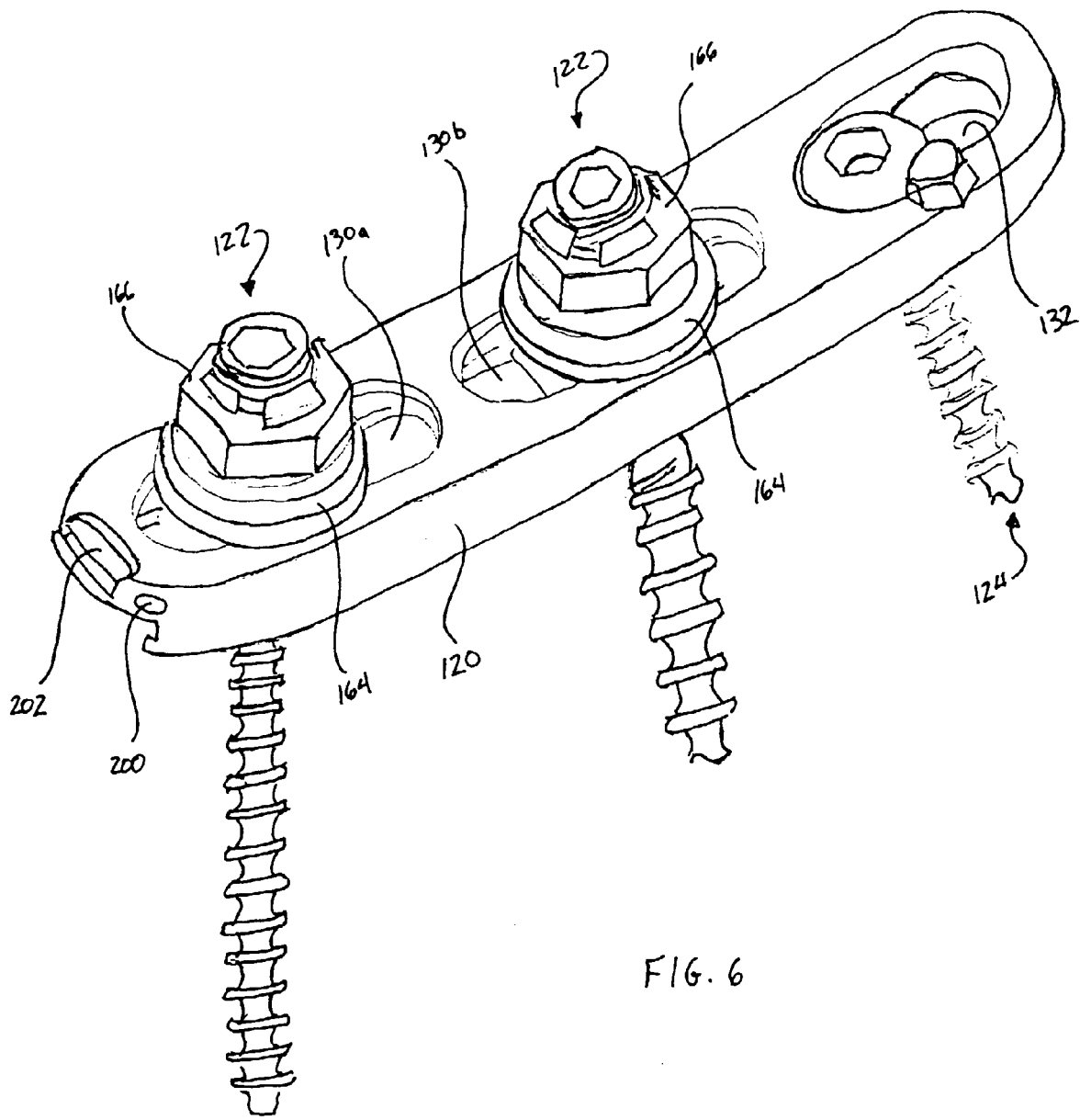
FIG. 6 is a perspective view of another embodiment of a device having features according to the present invention.

In another embodiment of the invention, shown in FIG. 6, plate member 120 is shown. Plate member 120 is similar in many respects to plate member 20, described above. However, plate member 120 is particularly useful in multi-level implantations (i.e., implantation over several respective vertebrae). Plate member 120 would include slots 130a and 130b, similar to slot 30 of plate member 20, and a slot 132, similar to slot 32 in plate member 20. Slots 130a and 130b are shown with fixation members 122, which are similar to fixation members 22 with plate member 20. A fixation member 124 that is similar to fixation member 24 described above is shown in slot 132. In use, pedicles for three vertebrae would be prepared as described above, each with a hole that may be tapped. The bolt portions of fixation members 124 would be inserted into the two most inferior vertebrae and plate member 120 placed over them so that they extend through slots 130a and 130b. Plate member 120 would then be positioned so that the hole in the superior-most pedicle is under slot 132. Washers 164 and nuts 166 are placed on bolts 160. The lower- or inferior-most fixation member 122 is then locked with respect to plate member 120 by tightening its respective nut 166. Fixation member 124 is then inserted through slot 132 and into the hole in the superior-most pedicle, and tightened as described above, to provide compression or distraction. The middle vertebra is allowed to float during the compression or distraction. Following the tightening of fixation member 124, the remaining fixation member 122 (attached to the middle vertebra) is locked with respect to plate member 120 by tightening its respective nut 166.

Plate member 120 also shows a transverse hole 200 and slot 202 at one end 134 of plate member 120. If desired, a pin (not shown) can be placed in hole 200 and through slot 202 to provide a way of holding or gripping plate member 120. The surgeon can use a gripping tool having teeth or a rounded opening, so that the teeth grip or the rounded opening surrounds such pin within hole 200 and slot 202. Plate member 120 (or plate member 20 if provided with a similar hole and/or slot and pin) can then be lowered into the surgical site while the surgeon holds onto the tool that grips plate member 120. If no pin is placed in hole 200, a proper gripping instrument could grip plate 120 at slot 202 (or plate member 20 if provided with a similar slot).

It will be appreciated that a plate member providing distraction can be formed in a similar fashion to that of plate member 20. As described above, plate member 20 includes a slot 32 with a sloping edge or surface 50. The downward slope of edge or surface 50 is generally from a point near the end 34 of plate member 20 toward the middle of plate member 20. A distraction plate, conversely, could include a sloped edge or surface that slopes generally upward from a point near the end 34 of plate member 20 toward the middle of plate member 20. Thus, as a fixation member 24 is tightened in such a distraction plate, the distraction plate would slide with respect to fixation member 24 such that the instrumented vertebrae would be pushed apart from each other, providing distraction.

It will further be appreciated that the embodiments described above should be made of materials suitable for implantation within the human or other body, and may consist of inert metals like titanium or stainless steel. Other sturdy materials such as certain ceramics or plastics may also be considered. Bio-resorbable materials, such as polylactic acid compounds, may be used along with or as a part of the parts described above.

As noted above, the bone fixation element 22 and 122 is described herein as the structures shown in U.S. Pat. Nos. 6,280,445 and 6,315,779, the entire disclosures of which are incorporated herein by reference. As indicated in those patents, such bone fixation elements allow multi-axial positioning of the plate member 20 with respect to the fixation element 22. This allows for further freedom in plate positioning and spinal correction via a minimally-invasive incision. It will be appreciated, however, that other known fixation elements may be used in place of the described fixation elements 22, 122, 24, and 124. Further, while slot 30 is described above as bottom-loading and slot 32 as top-loading, it will be seen that with variations in plate member 20 and/or differing fixation elements the slots may be loaded each from the same direction, or slot 30 may be loaded from the top and slot 32 from the bottom.

Additionally, the methods and structures described above have been generally noted as effective in minimally-invasive surgical procedures, i.e. those in which one or more relatively small holes are opened through the skin and to the surgical site. It will be appreciated that the methods and structures described above can also be used in other types of surgical procedures, such as open procedures.

It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

What is claimed is:

1. A method comprising:
   providing first and second sets of at least one plate member each having a curvature, a first slot, a second slot and a sloped surface within said second slot, said surface sloping in a longitudinal direction, and wherein each plate member in said first set has a first end portion and a middle portion, and said second slot has a first end adjacent said first end portion and a second end adjacent said middle portion, and wherein said surface slopes generally downward as it runs toward said second end of said slot, and wherein each plate member in said second set has a first end portion and a middle portion, and said second slot has a first end adjacent said first end portion and a second end adjacent said middle portion, and wherein said surface slopes generally upward as it runs toward said second end of said slot;
   selecting a plate member from one of said first and second sets;
   engaging a first anchoring member to a first vertebra;
   inserting said selected plate member into a patient proximate to first and second vertebrae to which said plate member is intended to be attached;
   placing said first slot over the first anchoring member engaged to the first vertebra;
   placing a second anchoring member through said second slot and into a second vertebra; and
   tightening the second anchoring member against said sloped surface so that said selected plate member moves with respect to said second anchoring member.

2. The method of claim 1, wherein said first anchoring member is tightened with respect to said selected plate member prior to said step of tightening the second anchoring member.

3. The method of claim 2, further comprising:
   loosening said first anchoring member and said second anchoring member;
   adjusting said selected plate member with respect to the vertebrae; and
   retightening said first anchoring member and said second anchoring member.

4. The method of claim 2, wherein said tightening of said second anchoring member causes one of compression and distraction of vertebrae.

5. The method of claim 4, further comprising ceasing said tightening of said second anchoring member when a predetermined amount of one of compression and distraction of vertebrae has occurred.

6. The method of claim 1, further comprising the step of preparing a minimally-invasive opening in the patient, and wherein said inserting step is performed through said minimally-invasive opening.

7. A method of minimally-invasively implanting a spinal implant, comprising:
   providing first and second sets of at least one plate member each having a curvature, a first slot, a second slot and a sloped surface within said second slot, said surface sloping in a longitudinal direction, and wherein each plate member in said first set has a first end portion and a middle portion, and said second slot has a first end adjacent said first end portion and a second end adjacent said middle portion, and wherein said surface slopes generally downward as it runs toward said second end of said slot, and wherein each plate member in said second set has a first end portion and a middle portion, and said second slot has a first end adjacent said first end portion and a second end adjacent said middle portion, and wherein said surface slopes generally upward as it runs toward said second end of said slot;
   selecting a plate member from one of said first and second sets;
   making one or more minimally-invasive openings proximate to first and second vertebrae in a patient;
   preparing a first hole in said first vertebra and a second hole in said second vertebra through at least one of said openings;
   inserting a first fixation member through one of said openings and into said first hole;
   inserting said selected plate member through one of said openings and into a position adjacent said vertebrae such that said first fixation member captures said selected plate member between portions of said first fixation member in said first slot of said selected plate member and said second slot of said selected plate member is adjacent said second hole;

inserting a second fixation member through one of said openings and through said second slot and into said second hole; and tightening said second fixation member such that said second fixation member and said second vertebra move with respect to said selected plate member.

8. The method of claim 7, further comprising:

preparing a third hole in a third vertebra through at least one of said openings, said third vertebra being between said first and second vertebrae;

inserting a third fixation member through one of said openings and into said third hole; and wherein said selected plate member has at least three slots and inserting said selected plate member is performed such that said third fixation member is within a third of said slots.

9. A kit, comprising:

one or more plate members having a curvature, a first slot, a second slot and a sloped surface within said second slot, said surface sloping in a longitudinal direction, said plate members being sized to be inserted into the body through a minimally-invasive opening;

at least one first bone fixation element, each adapted to engage at least one of said plate members and each having at least a part capable of being within said first slot; and at least one second bone fixation element, each adapted to engage at least one of said plate members along said sloped surface;

further comprising first and second sets of at least one plate member each, and wherein:

each plate member in said first set has a first end portion and a middle portion, and said second slot has a first end adjacent said first end portion and a second end adjacent said middle portion, and wherein said surface slopes generally downward as it runs toward said second end of said slot; and each plate member in said second set has a first end portion and a middle portion, and said second slot has a first end adjacent said first end portion and a second end adjacent said middle portion, and wherein said surface slopes generally upward as it runs toward said second end of said slot.

10. The kit of claim 9, comprising a plurality of said plate members, and wherein not all of said plate members are the same size.

11. The kit of claim 9, comprising a plurality of said plate members, and wherein not all of said plate members have the same curvature.

12. The kit of claim 9, comprising a plurality of said plate members, and wherein each of said plate members is configured for attachment to the spine in one or more of the cervical, thoracic, lumbar, and sacral regions.

13. The kit of claim 9, comprising a plurality of said first bone fixation elements, and wherein each of said first bone fixation elements is adapted for attachment to the spine in one or more of the cervical, thoracic, lumbar, and sacral regions.

14. The kit of claim 9, comprising a plurality of said second bone fixation elements, and wherein each of said second bone fixation elements is adapted for attachment to the spine in one or more of the cervical, thoracic, lumbar, and sacral regions.

15. An apparatus comprising:

a surgically implantable spinal plate member having a longitudinal axis, said plate member having a first elongated slot and a second elongated slot each substantially parallel to said axis;

said first slot having a side wall sized to accommodate at least a portion of a bone anchor;

said second slot having a side wall sized to accommodate at least a portion of a bone anchor;

a sloped surface within said second slot, said surface sloping in a longitudinal direction and substantially parallel to said longitudinal axis from one end of said second slot to an opposite end of said second slot, wherein said ends of said second slot are spaced from one another in said longitudinal direction;

a first bone fixation element adapted to engage said plate member, wherein at least a part of said first bone fixation element within said first slot with said plate engaged between first and second portions of said first bone fixation element; and a second bone fixation element adapted to engage said plate member within said second slot along said sloped surface, whereby tightening said second bone fixation element after engagement with said surface causes said plate member to move with respect to the second bone fixation element, wherein said plate member has a first end portion and a middle portion, and said second slot has a first end adjacent said first end portion and a second end adjacent said middle portion, and wherein said surface slopes generally upward as it runs toward said second end of said slot.

16. A kit, comprising:

one or more plate members extending along a longitudinal axis and having a curvature, a first slot, a second slot and a sloped surface within said second slot and located between top and bottom surfaces of said one or more plate members, said surface sloping in a longitudinal direction paralleling said longitudinal axis from one end of said second slot to an opposite end of said second slot, wherein said ends of said second slot are spaced from one another in said longitudinal direction;

at least one first bone fixation element, each adapted to engage at least one of said plate members and each having at least a part engaging said plate therebetween that extend from said first slot and along top and bottom surfaces of said plate member adjacent to said first slot; and at least one second bone fixation element, each adapted to engage at least one of said plate members along said sloped surface and further comprising first and second sets of at least one plate member each, and wherein each plate member in said first set has a first end portion and a middle portion, and said second slot has a first end adjacent said first end portion and a second end adjacent said middle portion, and wherein said surface slopes generally downward as it runs toward said second end of said slot; and each plate member in said second set has a first end portion and a middle portion, and said second slot has a first end adjacent said first end portion and a second end adjacent said middle portion, and wherein said surface slopes generally upward as it runs toward said second end of said slot.

17. An apparatus comprising:

a surgically implantable spinal plate member having a longitudinal axis, said plate element having a first elongated slot and a second elongated slot each substantially parallel to said axis and opening at a top surface and a bottom surface of said plate;

said first slot having a side wall sized to accommodate at least a portion of a bone anchor;

said second slot having a side wall sized to accommodate at least a portion of a bone anchor;

an edge between said top and bottom surfaces of said plate that extends around said second slot, said edge including a sloped surface within said second slot, said sloped surface sloping in a longitudinal direction along said second slot, said sloped surface being located a first distance below said top surface of said plate member at a first location along said second slot and said sloped surface being located a second greater distance below said top surface of said plate member at a second location along said second slot;

a first bone fixation element adapted to engage said plate member, wherein at least a part of said first bone fixation element is within said first slot; and a second bone fixation element adapted to engage said plate member within said second slot along said sloped surface, whereby tightening said second bone fixation element after engagement with said surface causes said plate member to move with respect to the second bone fixation element, wherein said plate member has a first end portion and a middle portion, and said second slot has a first end adjacent said first end portion and a second end adjacent said middle portion, and wherein said sloped surface slopes generally in a direction generally parallel to said longitudinal axis from said bottom surface of said plate toward said top surface of said plate as it runs toward said second longitudinal end of said slot, wherein said first and second ends are spaced from one another in said direction generally parallel to said longitudinal axis.

18. The apparatus of claim 17, wherein said surface slopes approximately linearly.

19. The apparatus of claim 17, further comprising a bone fixation element retainer connected to said plate member adjacent to said second slot.

20. The apparatus of claim 17, further comprising a third slot sized to accommodate at least a portion of a bone anchor.

21. The apparatus of claim 17, wherein said sloped surface extends along the longitudinal axis from one end of said edge to an opposite end of said edge.

* * * * *

UNITED STATES PATENT AND TRADEMARK OFFICE
CERTIFICATE OF CORRECTION

PATENT NO. : 7,608,096 B2
APPLICATION NO. : 10/385396
DATED : October 27, 2009
INVENTOR(S) : Foley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this

Twelfth Day of October, 2010

David J. Kappos
*Director of the United States Patent and Trademark Office*